US009510787B2

(12) United States Patent
Kniazev et al.

(10) Patent No.: US 9,510,787 B2
(45) Date of Patent: Dec. 6, 2016

(54) METHOD AND SYSTEM FOR RECONSTRUCTING SAMPLED SIGNALS

(71) Applicant: Mitsubishi Electric Research Laboratories, Inc., Cambridge, MA (US)

(72) Inventors: Andrei Kniazev, Cambridge, MA (US); Akshay Gadde, Los Angeles, CA (US); Dong Tian, Boxborough, MA (US); Hassan Mansour, Boston, MA (US); Richard C Waters, Concord, MA (US)

(73) Assignee: Mitsubishi Electric Research Laboratories, Inc., Cambridge, MA (US)

( * ) Notice: Subject to any disclaimer, the term of this patent is extended or adjusted under 35 U.S.C. 154(b) by 70 days.

(21) Appl. No.: 14/567,015

(22) Filed: Dec. 11, 2014

(65) Prior Publication Data
US 2016/0173736 A1 Jun. 16, 2016

(51) Int. Cl.
*A61B 5/00* (2006.01)
*G01R 33/561* (2006.01)
(Continued)

(52) U.S. Cl.
CPC .............. *A61B 5/72* (2013.01); *A61B 5/0035* (2013.01); *A61B 5/7257* (2013.01);
(Continued)

(58) Field of Classification Search
CPC ... A61B 5/0035; A61B 5/7257; A61B 5/0073; A61B 5/7235; A61B 5/72; G01R 33/5611; G01R 33/5608; G06T 11/003; G06T 11/006; G06T 11/005; G06T 2207/20064; G06T 2207/10081; G06T 2207/20048; G06T 2207/20072; G06T 2207/20076; G06T 2211/421; G06T 7/206; G06T 9/00; G10L 19/008; G10L 19/03; G10L 19/24; G03H 2001/0883; G03H 2240/62; G06K 9/0057; G06K 9/527; G06K 9/6232; G06K 9/6262; G06K 9/78; G01N 23/046; G01N 29/0654; G01N 29/46; H04N 19/00; H04N 19/122; H04N 19/156; H04N 19/172; H04N 19/395; H04N 19/61; H04N 19/63; H04N 19/91; H04N 5/142
See application file for complete search history.

(56) References Cited

U.S. PATENT DOCUMENTS 4,209,843 A * 6/1980 Hyatt ................... B60R 16/0373
708/422
4,581,715 A * 4/1986 Hyatt ................... B60R 16/0373
708/403
(Continued)

OTHER PUBLICATIONS

Bansal et al., "Bandwidth expansion of narrowband speech using non-negative matrix factorization," In Ninth European Conference on Speech Communication and Technology, 2005.
(Continued)

*Primary Examiner* — Manav Seth
(74) *Attorney, Agent, or Firm* — Gene Vinokur; James McAleenan; Hironori Tsukamoto

(57) ABSTRACT

A method reconstructs a signal by sampling the signal using a sampling procedure to obtain an input signal. A consistent set is determined from the input signal including the first elements such that applying the sampling procedure to the first elements results in the input signal. According to the type of the signal, a guiding set is determined including second elements disjoint from the first elements. A reconstruction set including third elements is generated so that the third elements minimize a sum of a first similarity measure
(Continued)

of the third elements to the second elements and a second similarity measure of the third elements to the first elements. A transformed signal that minimizes a function on the reconstruction set is determined. A reconstructed signal is rendered so that a third similarity measure of the reconstructed signal to the transformed signal is smaller than a tolerance.

20 Claims, 10 Drawing Sheets

(51) Int. Cl.
G06T 11/00 (2006.01)
H04N 19/00 (2014.01)
G06K 9/00 (2006.01)
G06K 9/52 (2006.01)
G06F 17/17 (2006.01)
G06T 3/40 (2006.01)
G10L 21/00 (2013.01)

(52) U.S. Cl.
CPC .......... *G01R 33/5611* (2013.01); *G06F 17/17* (2013.01); *G06K 9/0057* (2013.01); *G06K 9/527* (2013.01); *G06T 3/40* (2013.01); *G06T 11/003* (2013.01); *G10L 21/00* (2013.01); *H04N 19/00* (2013.01)

(56) References Cited

U.S. PATENT DOCUMENTS

| | | | |
|---|---|---|---|
| 4,774,565 A | 9/1988 | Freeman | |
| 4,928,251 A * | 5/1990 | Marzalek | G01R 23/02 324/76.39 |
| 5,587,711 A | 12/1996 | Williams et al. | |
| 5,748,507 A | 5/1998 | Abatzoglou et al. | |
| 6,751,363 B1 * | 6/2004 | Natsev | G06K 9/522 358/403 |
| 7,191,123 B1 * | 3/2007 | Bessette | G10L 19/083 704/206 |
| 7,245,755 B1 * | 7/2007 | Pan | A61B 6/583 378/4 |
| 7,272,556 B1 * | 9/2007 | Aguilar | G10L 19/093 704/201 |
| 7,403,875 B2 * | 7/2008 | Vogel | H03M 1/0836 702/189 |
| 7,424,088 B2 * | 9/2008 | Zamyatin | G06T 11/005 378/15 |
| 7,444,011 B2 * | 10/2008 | Pan | A61B 6/5288 378/4 |
| 7,684,846 B2 * | 3/2010 | Johnson | A61B 5/05 181/101 |
| 7,841,982 B2 * | 11/2010 | Johnson | A61B 5/0507 181/101 |
| 8,121,245 B2 * | 2/2012 | Pan | A61B 6/032 378/2 |
| 8,204,325 B2 * | 6/2012 | Segall | G06T 9/001 382/243 |
| 9,047,865 B2 * | 6/2015 | Aguilar | G10L 19/093 |
| 2006/0287596 A1 * | 12/2006 | Johnson | A61B 5/4312 600/437 |
| 2008/0052068 A1 * | 2/2008 | Aguilar | G10L 19/093 704/230 |
| 2009/0185747 A1 * | 7/2009 | Segall | G06T 9/001 382/220 |
| 2012/0150544 A1 | 6/2012 | McLoughlin et al. | |
| 2012/0188368 A1 | 7/2012 | Shechtman et al. | |
| 2014/0232581 A1 | 8/2014 | Nguyen et al. | |
| 2015/0187052 A1 * | 7/2015 | Amroabadi | A61B 6/5205 382/131 |
| 2015/0192653 A1 * | 7/2015 | Sharif | A61B 5/055 600/420 |

OTHER PUBLICATIONS

Berger et al, Sampling and reconstruction in different subspaces by using oblique projections. Technical Report arXiv:1312.1717 [math.NA], Dec. 2013.
Eldar, Sampling with arbitrary sampling and reconstruction spaces and oblique dual frame vectors. Journal of Fourier Analysis and Applications, 9(1):77-96, 2003.
Eldar et al., "Beyond bandlimited sampling," Signal Processing Magazine, IEEE, 26(3):48-68, 2009.
Narang et al., "Signal processing techniques for interpolation in graph structured data," In IEEE International Conference on Acoustics, Speech and Signal Processing (ICASSP), pp. 5445-5449, 2013.
Narang et al., Localized iterative methods for interpolation in graph structured data. In Global Conference on Signal and Information Processing (GlobalSIP), 2013 IEEE, pp. 491-494, Dec. 2013.
Unser et al. A general sampling theory for nonideal acquisition devices. Signal Processing, IEEE Transactions on, 42(11):2915-2925, 1994.

* cited by examiner

METHOD AND SYSTEM FOR RECONSTRUCTING SAMPLED SIGNALS

FIELD OF THE INVENTION

This invention relates generally to signal reconstruction, and more particularly to analyzing, approximating, denoising and interpolating sampled signals.

BACKGROUND OF THE INVENTION

Signal reconstruction is used in many signal processing applications, and under various names. In image and video processing, a signal can comprise, e.g., an image, and a goal of the reconstruction can be, e.g., outputting an image at super-resolution, i.e., at a resolution that is higher than an original resolution of the image. Similarly, in audio processing applications, a signal can comprise an audio sequence, wherein the reconstruction can be used, e.g., to increase audio frequency ranges. In data mining applications, signal reconstruction appears in a form of, e.g., data completion. Signal reconstruction, and more particularly analyzing, approximating, denoising and interpolating sampled signals, is practically important and described in numerous patents and publications.

A method and apparatus for waveform reconstruction for sampled signal edges of a repetitive signal data system is disclosed in U.S. Pat. No. 4,928,251. A sequence of relatively low resolution samples of a repetitive input signal with high frequency components is acquired, without triggering, to determine an approximate waveform from the low resolution samples. Then, a fast Fourier transform is applied to a reconstructed time record of the input signal to obtain a frequency for each signal component. The sampled waveform is reconstructed by overlaying sampled components with reference to a common time or phase.

A system for reconstruction of non-uniformly sampled signals is disclosed in U.S. Pat. No. 7,403,875. The non-uniformly sampled signal includes a sampled signal and an amplitude error between the signal sampled with an equidistant sample period and the non-uniformly sampled signal. A reconstructed amplitude error is determined through a time offset and the non-uniformly sampled signal. The amplitude error is subtracted from the non-uniformly sampled signal.

A method and system for super-resolution signal reconstruction from an input field is disclosed in U.S. publication 20120188368. The method comprises: providing measured data corresponding to output field of the measurement system; providing data about sparsity of the input field, and data about effective response function of the measurement system; and processing the measured data based on the known data. The processing first determines a sparse vector as a function of the measured data, along with a set indicating the sparsity of the input field, and the effective response function. The sparse vector is then used for reconstructing the input information.

U.S. Pat. No. 4,774,565 discloses a method for sensing scene light and providing sampled image data in three colors. The sampled image data is subsequently interpolated for the non-sampled colors and thereafter subtracted to provide two color difference signals. The two color difference signals, in turn, are each median filtered and subsequently reconstructed in conjunction with the originally sampled image data to reduce the color fringing in the reconstructed image.

A real-time super-resolution method is disclosed in U.S. Pat. No. 5,748,507. In that method, a super-resolution technique of constrained total least squares is used to extend samples of input signals for higher resolution spectral analysis and output.

A reconstruction method using a Hilbert transform is disclosed in U.S. Pat. No. 7,424,088. The method determines an image data value at a point of reconstruction in a computed tomography (CT) image of a scanned object, filtering the obtained projection data with a one-dimensional ramp filter to generate ramp-filtered data, and applying a backprojection operator with inverse distance weighting to the ramp-filtered data to generate the image data value at the point of reconstruction in the CT image.

A method for reconstruction of sparse frequency spectrum from ambiguous under-sampled time domain data is disclosed in U.S. publication 20140232581. The method converts a high bandwidth analog signal to a digital signal. The method splits a high bandwidth analog signal into parallel channels with increasing delays. Each channel is then sampled at a sub-Nyquist frequency smaller than the high bandwidth signal. The channels are then upsampled at the Nyquist frequency of the high bandwidth signal and combined to generate a digital signal representing the high bandwidth analog signal.

A method for reconstructing signals from inaccurate measurements due to quantization is disclosed in U.S. Pat. No. 5,587,711. Non-linear filtering is applied to a quantized signal to distribute quantum changes over their respective time intervals to provide, for example, a smoother reconstructed signal. The quantization bounds are enforced for each refined signal point to ensure a reconstructed signal that is within the bounded uncertainty associated with the original signal.

U.S. publication 20120150544 discloses a method for reconstructing speech from an input signal comprising whispers. The method analyses the input signal to form a representation of the input signal that is then modified to adjust the spectrum of the signal. The modification changes the bandwidth of at least one formant in the spectrum to achieve a predetermined spectral energy distribution and amplitude for the at least one formant.

Sampling theories are important for signal processing systems and applications, such as generating super-resolution images, processing biomedical imaging, sampling rate conversion for acoustic signals, and graph based signal interpolation.

One example is the reconstruction of band-limited signals from samples acquired in the time domain, see Unser et al. "A general sampling theory for non-ideal acquisition devices," Signal Processing, IEEE Transactions on, 42(11): 2915-2925, 1994. Several extensions of a Shannon-Hartley theorem are developed based on viewing sampling in a broader sense of a projection onto appropriate subspaces and then selecting the subspaces according to specific applications; see Eldar et al., "Beyond bandlimited sampling," Signal Processing Magazine, IEEE, 26(3):48-68, 2009.

More recently, the reconstruction of signals on graphs, band-limited with respect to eigenvalues of the graph Laplacian, from signal samples on a subset of nodes of the graph has gained popularity, e.g., see Narang et al., "Signal processing techniques for interpolation in graph structured data," IEEE International Conference on Acoustics, Speech and Signal Processing (ICASSP), pp. 5445-5449, 2013, and Narang et al., "Localized iterative methods for interpolation in graph structured data," Global Conference on Signal and Information Processing (GlobalSIP), 2013 IEEE, pages 491-494, December 2013.

One task of the reconstruction is to determine a reconstructed signal of an unknown original signal based on samples of the original signal, where the samples typically belong to a sampling subspace; see Eldar et al., "Beyond bandlimited sampling," Signal Processing Magazine, IEEE, 26(3):48-68, 2009. Searching for reconstructed signals is commonly performed in a subspace. We refer to the subspace as a guiding subspace. It is often desired to minimize an error, expressed as distance between the unknown original signal and the reconstructed signal.

In one prior art method, a consistent reconstruction method is disclosed. A consistency condition ensures that the reconstructed signal always yields the same samples in the sampling subspace as the original signal. In addition, it is required that the direct sum of the guiding subspace and the complement of the sampling subspace is equal to the signal space so that an oblique projector can be used in the solution, see Eldar, "Sampling with arbitrary sampling and reconstruction spaces and oblique dual frame vectors," Journal of Fourier Analysis and Applications, 9(1):77-96, 2003, and Berger et al, "Sampling and reconstruction in different subspaces by using oblique projections," Technical Report arXiv:1312.1717, December 2013. The requirement that the direct sum of the guiding subspace and the complement of the sampling subspace are equal to the signal space is too restrictive for some applications or can be disadvantageous, e.g., the requirement can lead to oblique projectors with large norms, resulting in unstable reconstruction methods that are very sensitive to signal noise.

To circumvent this requirement, a more general constrained reconstruction minimizes a distance from the reconstructed signal to the sample-consistent reconstruction plane. If the distance is zero, then this reconstruction is sample consistent, otherwise, the reconstruction represents a generalized reconstruction. In most practical applications, all possible consistent reconstructed signals are disjoint from the guiding subspace. Those generalized reconstruction methods place the reconstructed signal into the guiding subspace, making it sample inconsistent, see Berger et al, "Sampling and reconstruction in different subspaces by using oblique projections," Technical Report arXiv: 1312.1717, December 2013.

In a different application area, a bandwidth expansion of a narrowband audio signal, a reconstruction method makes the reconstructed signal consistent, see Bansal et al., "Bandwidth expansion of narrowband speech using non-negative matrix factorization," Ninth European Conference on Speech Communication and Technology, 2005. Rather than placing the reconstructed signal into the guiding subspace as in Berger et al.

One of key limitation of the prior art signal reconstruction methods is that in practice it may not be clear a priori if the reconstructed signal should be forced into the guiding subspace, or whether the reconstructed signal should be sample consistent, in a practically important case, where the guiding subspace contains no sample consistent signals. The prior art does not cover a situation where, e.g., both procedures, sampling and guiding, can be equally reliable.

SUMMARY OF THE INVENTION

The embodiments of the invention provide a method and system for reconstructing a signal of a certain type from an input signal obtained using a sampling procedure. A consistent set is determined from the input signal that includes first elements such that applying the sampling procedure to the first elements of the consistent set results in the input signal.

Sampling typically involves loss of information. Therefore, to recover the generally unknown original signal, assumptions are needed. One such assumption may be that the signal belongs to a closed guiding set. The guiding set is determined according to the type of the signal containing second elements that are disjoint from the first elements of the consistent set. The guiding set of the signal can be determined using a model or other form of description of desirable reconstructed signal behavior, e.g., learned from training datasets. For signals with natural spectral properties, spectral transforms, e.g., Fourier, cosine, and wavelet transforms, can be used to transform signals into a spectral domain, where the guiding subspace can be chosen as corresponding to certain frequency ranges, e.g., assuming that the desired signal is band-limited.

For signals without self-evident spectral properties, the signals are embedded into a specially constructed structure, depending on a type of the signal, e.g., a graph, or a Riemannian manifold, wherein spectral properties are determined by an "energy" norm and its "energetic" operator, e.g., graph Laplacian, or Laplace-Beltrami operator, correspondingly. The guiding subspace can then be chosen as an invariant subspace of the energetic operator, corresponding to certain ranges in its spectrum, e.g., assuming that the desired signal is band-limited, having components primarily from the low part of the spectrum of the energetic operator. The embedding also involves choosing a distance in the embedded space, depending on a signal similarity measure in the signal space, which can comprise, e.g., correlation, coherence, divergence, or metric, depending of the type of the signal.

In one embodiment of the invention, the type of the input signal comprises an image, a patch in an image, a set of images, a video sequence, a patch in a video sequence, a depth map, a spectral map, a patch of a depth map, a patch of a map, image-related feature vectors, and combinations thereof. A goal of the image-based reconstruction can be, e.g., image super-resolution, upscaling, inpainting, depth recovery, increasing image dynamic range, adding video frames for faster refresh rate. Some seemingly unrelated tasks can be framed as image-based signal reconstruction problems, e.g., classification, i.e., determining missing labels, or object tracking and future movement prediction in a video sequence, i.e., obtaining missing or future values of an indicator function of the object.

In another embodiment, the signal further includes a sound field and wherein the type of the input signal includes one or a set of audio sequences, patches in audio sequences, audio spectral maps, patches of audio spectral maps, audio feature vectors, and combinations thereof. Audio-based reconstruction can be used, e.g., for upsampling, increasing audio frequency or dynamic ranges, adding synthetic audio channels, depth reconstruction, and audio restoration, including, e.g., real-time removal of impulse noise. A combination of image- and audio-based signal reconstruction problems can be beneficial, e.g., for automatic lip reading and to reconstruct missing or corrupted audio in audio-video sequence, by analyzing the corresponding available video frames.

For the above type of input signals, the guiding set is determined using a group comprising one or a combination of a Fourier transform, a cosine transform, a wavelet transform, a method for learning from a training dataset, and a spectral transform of a matrix of a graph, wherein the graph is constructed according to the type, and the matrix of the graph is determined using the graph and the input signal.

In data mining applications, signal reconstruction appears in a form of, e.g., data completion or interpolation, estimating missing data predicting future data. For example, time series data reconstruction can be used to deal with faulty sensors, and data extrapolation can help to predict a future system failure. Such a reconstruction can, e.g., also involve audio-video signals from a camera pointing at the system.

In yet another embodiment, one or a combination of the type, the consistent set, and the guiding set is determined using a first set of probability distributions, and the reconstruction set is determined using a second probability distribution using a statistical similarity measure between stochastic random variables according to the first set of probability distributions. Using probability distributions is beneficial, e.g., when the sampling procedure results in measurements that are randomly distributed, for example, the measurements include Gaussian noise or when the guiding set is learned from stochastic random variables, describing desired properties of the reconstructed signal. Then, the reconstruction set also includes stochastic random variables.

In another embodiment of the invention, it is beneficial to generate the reconstructed signal in real time, e.g., when the input signal is streaming.

We are interested in the practically important case, where the guiding set contains no sample consistent signals. Thus, it is impossible to satisfy the conditions that the reconstructed signal belongs to the guiding set and is sample consistent at the same time.

In that case, the prior art suggests only two alternative choices for the reconstruction: to be in the guiding set or to be sample consistent. Our invention is based on realization that these two alternatives can be interpreted as extreme choices from a novel concept of a reconstruction set. The reconstruction set contains third elements such that the third elements minimize a sum of a first similarity measure of the third elements to the second elements set (i.e., the guiding set) and a second similarity measures of the third elements to the first elements set (i.e., the consistent set). The reconstruction set thus describes the shortest, in terms of the chosen similarity measure, pathway set between the guiding set and the consistent set for the given sampled signal. If it is not known, which one of the procedures, sampling or guiding, can result in a better representation of the reconstructed signal, then our realization is that any element of the reconstruction set becomes a valid candidate for reconstruction.

Having to output the complete reconstruction set of multiple reconstructed signals may not be appropriate in some applications. To select a single reconstructed signal from the reconstruction set, one needs additional information, for example, a function that represents a ratio of the reconstruction cost over the reconstruction quality.

In one embodiment, a transformed signal is determined by minimizing the function on the reconstruction set and the reconstructed signal is then generated, so that a third similarity measure of the reconstructed signal to the transformed signal is smaller than a predetermined tolerance. Similarly, the reconstructed signal can be generated in a neighborhood of the reconstruction set that minimize the function according to another tolerance.

In a different embodiment, the reconstructed signal is generated to minimize a weighted sum of the function and a similarity measure to the reconstruction set, which is beneficial when the function value is more representative of the reconstructed signal than both the consistent and the guiding set. Minimizing the weighted sum of the function and the similarity measure to the reconstruction set relaxes the restriction of the reconstructed signal to the neighborhood of the reconstruction set.

In yet another embodiment of the invention, the transformed signal is determined using an iterative method that minimizes the function. The iterative method can have an adjustable termination criterion determined using a training dataset. The iterative method can be determined using a conjugate gradient iterative method, a Chebyshev iterative method, or a preconditioned iterative method.

In one embodiment of the invention, one or a combination of the consistent set and the guiding set comprises one or a group of linear sets. The reconstruction set is determined using a linear set. One example of linear sets is a Krylov-based subspace selected from a group consisting of an approximate Krylov subspace, a rational Krylov subspace, and an approximate rational Krylov subspace.

DETAILED DESCRIPTION OF THE PREFERRED EMBODIMENTS

Figure 1:
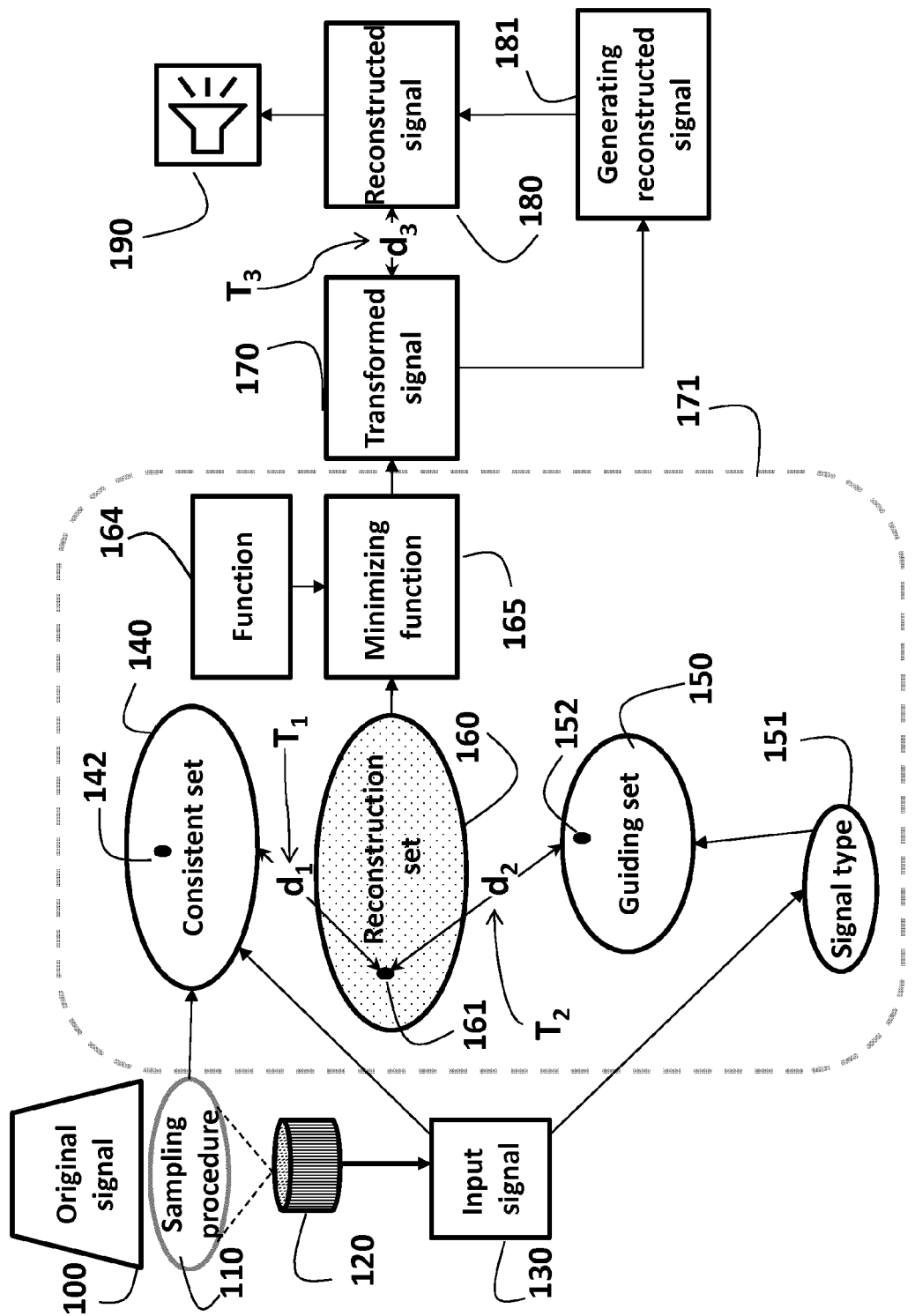
FIG. 1 is a schematic of a method and system for reconstructing a signal according to embodiments of the invention.

As shown in FIG. 1, embodiments of the invention provide a method and system for reconstructing an input signal 130 as a reconstructed signal 180. The input signal 130 is acquired by a sampling procedure 110 on an original signal 100 using a sensor 120. The input signal can be stored in memory of a processor or processed in real time. The input signal is associated with a type 151. The sampling procedure can operate in conjunction with, e.g., a sensor 120 of a camera, when the input signal is an image or a video sequence. Other sampling procedures 110 and sensors 120 can be designed for a particular signal type 151 of input signals 130 described in greater detail below.

A consistent set 140 including first elements 142 is determined for the input signal 130, such that applying the sampling procedure 110 to any element 142 in the consistent set 140 results in the input signal 130. The consistent set 140 can also be stored in the memory.

A guiding set 150 including second elements 152, stored in the memory, is determined according to the type 151 of the input signal 130. The guiding set 150 is disjoint from the consistent set 140.

A reconstruction set 160 is also determined and stored. The reconstruction set 160 is composed of third elements 161, which minimize a sum of a first similarity measure $d_1$, within a first tolerance $T_1$, from the third elements 161 to the first elements 142, and a second similarity measure $d_2$, within a second tolerance $T_2$, from the third elements 161 to the second elements 152.

In one embodiment of the invention, the similarity measures are determined using one or a combination of a distance, a norm, a semi-norm, a correlation, a coherence, a divergence, and a metric, according to the type of the signal and the goal of the reconstruction. For example, a Euclidian 2-norm provides least squares minimization, and is beneficial in terms of computational costs of the method, as implemented in the processor. In another example, various weighted least squares norms can be used, with different weights chosen for different similarity measures, which is beneficial, allowing a user to control relative importance, e.g., of the first similarity measure of the third elements to the second elements set (i.e., the guiding set) compared to the second similarity measures of the third elements to the first elements set (i.e., the consistent set).

A function 164 is minimized 165 on the reconstruction set 160 to obtain a transformed signal 170.

The reconstructed signal 180 is generated 181 from the transformed signal 170 so that a third similarity measure $d_3$ between the reconstructed signal and the transformed signal 170 is smaller than a third tolerance $T_3$. In this way, the reconstructed signal is not in the consistent set 140 and not in the guiding set 150. The reconstructed signal can be provided to an output device 190 appropriate for the signal, e.g., a display unit or printer when the input signal includes images.

The steps of the method, leading to the transformed signal 170 from the input signal 130, can be viewed as transforming the input signal 130 to the transformed signal 170, using a transformation function 171.

Figure 2A:
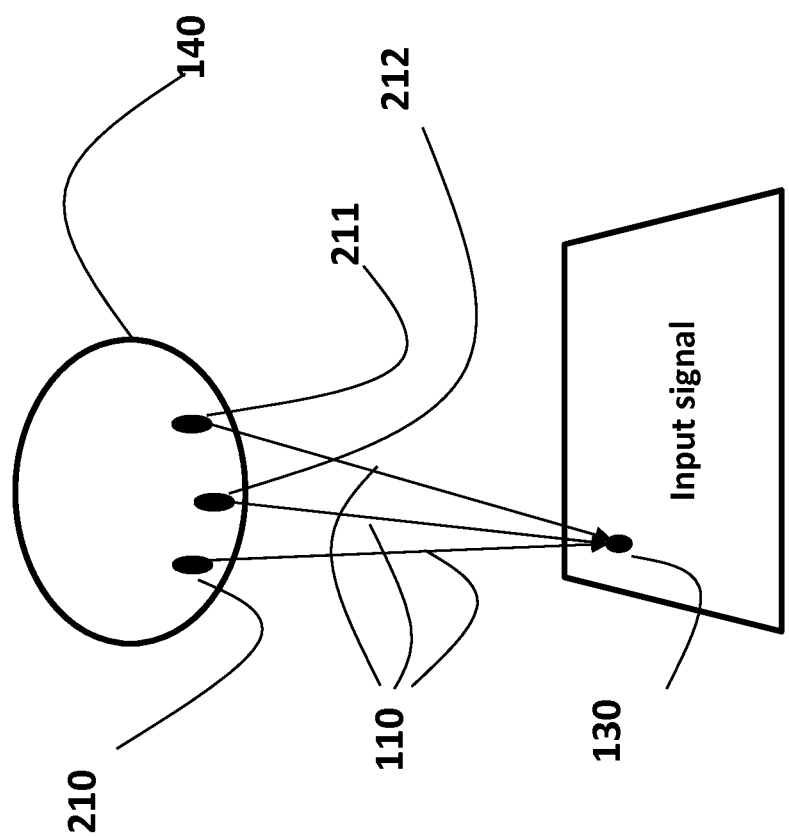
FIGS. 2A, 2B and 2C are schematics of a method for determining a reconstruction set according to embodiments of the invention.

FIG. 2A shows an embodiment of generating the consistent set 140 for the input signal 130 obtained by the sampling procedure 110. The consistent set contains first elements 210, 211, 212 which when sampled by the sampling procedure 110 result in the input signal. The elements in the consistent set can be generated by applying an adjoint of the sampling procedure to the input signal and any element in a null space of the sampling procedure.

Figure 2B:
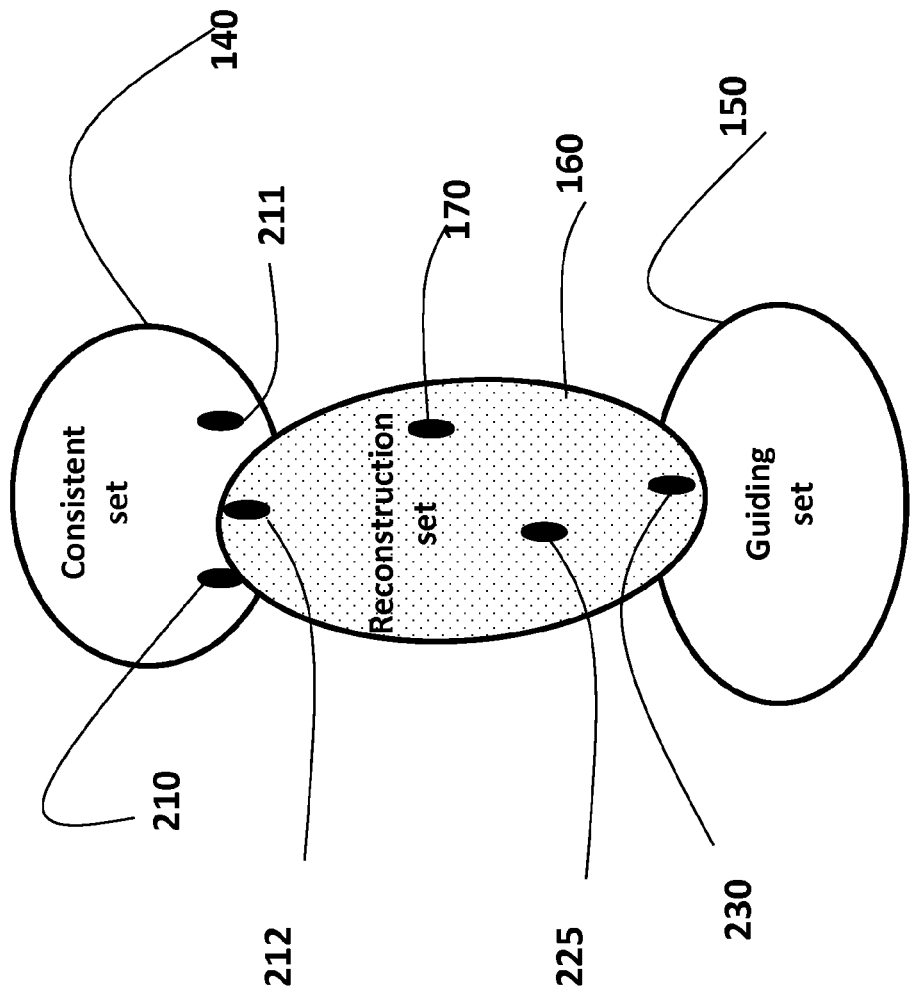

FIG. 2B shows an example relationship between the consistent set 140, the reconstruction set 160, and the guiding set 150. The reconstruction set 160 intersects the consistent set 140 for at least the first element 212 and the guiding set 150 for at least the second element 230. The reconstruction set can also contain third elements 225 which do not belong to either the consistent set or the guiding set, and which is different from the transformed signal 170.

Figure 2C:
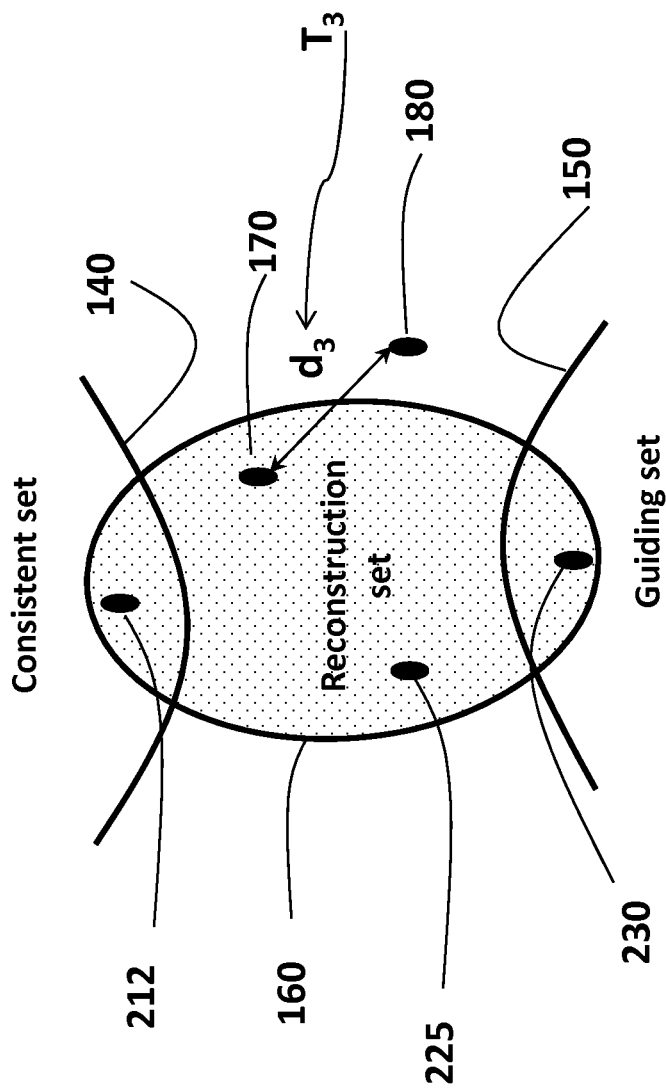

FIG. 2C shows an example of the relationship between the transformed signal 170 and the reconstructed signal 180. The reconstructed signal 180 is determined such that a third similarity measure $d_3$ of the reconstructed signal to the transformed signal 170 is smaller than the tolerance $T_3$.

Another embodiment of the invention provides a method for determining the transformation function 171 for determining a reconstructed signal 180 from an input signal 130. As before, the input signal, the consistent, guiding and reconstruction sets are stored in a memory of the system.

Figure 3:
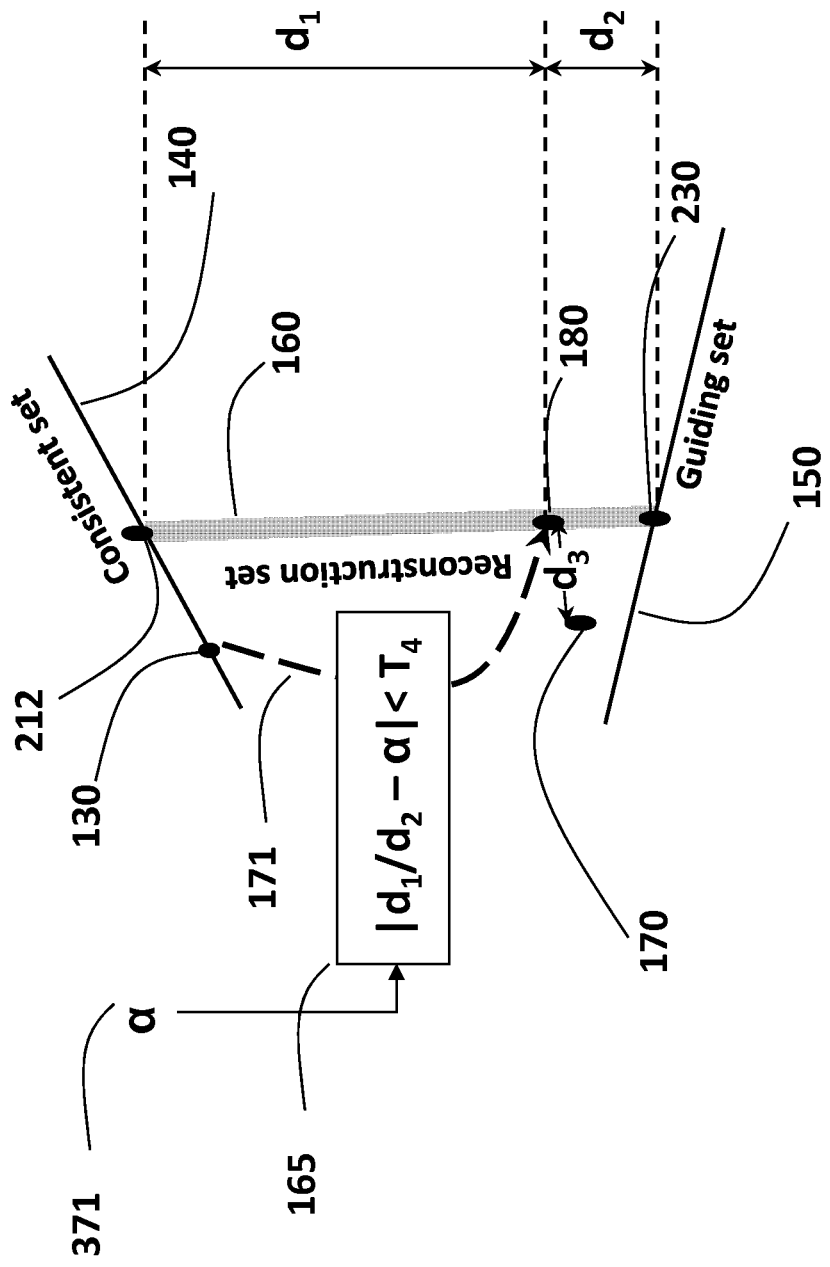
FIG. 3 is a schematic of a reconstruction set for three dimensional vector signals, where the consistent set and guiding set are lines according to embodiments of the invention.

As shown in FIG. 3 for one embodiment of the invention, one or a combination of the consistent set and the guiding set comprises one or a group of linear sets. The reconstruction set can determined using a convex subset of a linear set, e.g., an interval, as illustrated in FIG. 3. FIG. 3 shows an example embodiment of the invention wherein the consistent set, and the guiding set comprise a group of linear sets 140 and 150, and wherein the reconstruction set comprises a second linear set 160 connecting the linear sets in the first group, and thus describes the shortest, in terms of the chosen similarity measure, pathway set 160 between the guiding set 150 and the consistent set 140 for the given sampled signal 130.

Specifically, the reconstruction set in FIG. 3 is an interval 160 with a first endpoint 212 in the consistent set 140 and a second endpoint 230 in the guiding set 150. The reconstruction set 160 is determined as a convex linear combination of the first endpoint and the second endpoint. The transformed signal 180 is determined by the transformation function 171 that minimizes a function 164 in terms of a first similarity measure $d_1$ of the transformed signal to the first endpoint 212 and a second similarity measure $d_2$ of the transformed signal to the second endpoint 230. The minimization 165 is obtained when the ratio of a first similarity measure $d_1$ to a second similarity measure $d_2$ is within a tolerance $T_4$ of a parameter $\alpha$ 371.

In the case when the input signal 130 is inaccurate or noisy, the parameter $\alpha$ 371 can be defined as being proportional to the ratio of the inaccuracy in the input signal to a diameter of the reconstruction set 160, wherein the diameter of the reconstruction set 160 is determined using the similarity measure between the extreme opposite endpoints of the reconstruction set 160, e.g., between the first endpoint 212 in the consistent set 140 and the second endpoint 230 in the guiding set 150 in FIG. 3. Using the ratio of the inaccuracy in the input signal to the diameter of the reconstruction set is beneficial because the ratio allows the user to choose the parameter $\alpha$ according to the accuracy of the sampling procedure and reliability of the guiding set, which are known for many practical applications.

For example, the sampling procedure 110 involves an inaccuracy in the input signal 130, where the inaccuracy may appear due to one or a combination of noise, a limited accuracy of the sensor 120 providing the sampling procedure 110, and a limited precision of data representing the input signal 130. The accuracy of the sensor 120 may be known from sensor specifications. The precision of the data representing the input signal 130 is typically known in advance, being determined by data quantization for a number of bits available to store the data, as implemented on the processor connected to the memory.

In one embodiment, one or a combination of the type 151 of the signal, the consistent set 140, and the guiding set 150 are determined using a first set of probability distributions, for example, a Gaussian distribution or a mixture of Gaussian distributions. The reconstruction set is then determined using a second probability distribution using a statistical similarity measure between stochastic random variable according to the first set of probability distributions, such as a Kullback-Leibler (KL) divergence. In this case, the input signal 130 can represent samples from a statistical distribution.

One example assigns a Gaussian mixture model (GMM) to the pixels of a video sequence. The reconstruction task could be one of determining a video background from a sequence of streaming input images that have occlusions.

The guiding set 150 is then represented as the GMM that describes the distribution of background pixels in the video. The consistent set 140 includes all pixels that are known to be a part of the background. The reconstructed signal 180 is then the background scene represented in the video sequence with any foreground occlusions removed.

According to multiple embodiments, the guiding set 150 of the signal can be determined using a model or other form of description of desirable reconstructed signal behavior. In one embodiment, the guiding set 150 is learned a priori from training datasets, which is advantageous when training datasets containing the desirable reconstructed signal behavior are available, or the corresponding data for training can be collected, wherein the model of the desirable reconstructed signal behavior cannot be explicitly formulated.

For signals with natural spectral properties, spectral transforms, e.g., Fourier, cosine, and wavelet transforms, can be used to transform signals into a spectral domain, where the guiding set 150 can be chosen as corresponding to certain frequency ranges, e.g., assuming the model that the desired signal is band-limited. This spectral model is advantageous in many applications of signal processing, wherein signals can be naturally analyzed and well characterized by their spectral properties.

For signals without self-evident spectral properties, the signals can be embedded into a specially constructed structure, depending on a type 151 of the signal, e.g., a graph, or a Riemannian manifold, wherein spectral properties are determined by an "energy" norm and its "energetic" operator, e.g., graph Laplacian matrix, or Laplace-Beltrami operator, correspondingly. The guiding subspace 150 can then be chosen as an invariant subspace of the energetic operator, corresponding to certain ranges in its spectrum, e.g., assuming that the desired signal is band-limited, having components primarily from the low part of the spectrum of the energetic operator. The energetic operator can be constructed for a given signal 130, or a group of signals. The energetic operator also can be learned a priori from training datasets.

In one embodiment, the guiding subspace is determined for the energetic operator comprising a graph matrix constructed from a signal embedded into a graph, called a graph signal. The problem of reconstructing or interpolating a band-limited graph signal is similar to determining a signal that is at an intersection of a plane specified by known samples and a subspace spanned by low-frequency eigenvectors of the graph matrix. This problem can be reformulated as a linear system with a symmetric positive semi-definite matrix or operator; see "Problem Formulation" section below.

Figure 4:
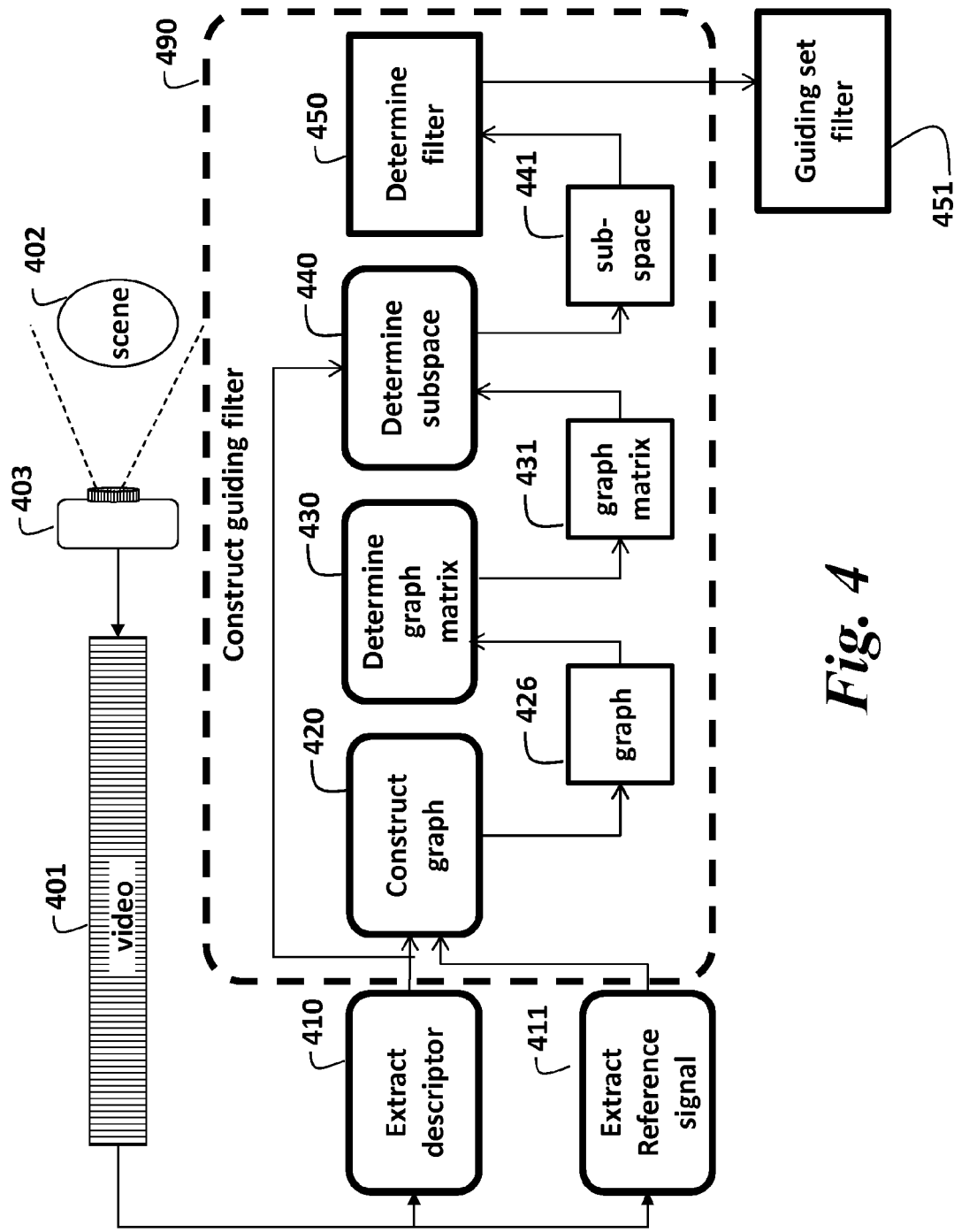
FIG. 4 is a schematic of the method and system for interpolating a graph signal according to embodiments of the invention.

FIG. 4 shows embodiments of the method and system for reconstructing or interpolating a graph signal. An input signal 130 (video sequence 401) is acquired of a scene 402 by a sensor 120 (camera 403). Descriptors (feature vectors) are extracted 410 and a referenced signal is extracted 411 from the input signal.

A graph 426 is constructed 420 using the data corresponding to the input signal 130. The input signal can be represented using feature vectors, as in a case of semi-supervised learning, or sampled pixels, as well as a reference signal as in the case in 3D view reconstruction. Nodes in the graph correspond to samples of the input signal 130 or pixels. The nodes are connected to a subset of the other nodes with weighted edges. The weights represent a similarity between the data associated with the nodes connected by the edges.

Figure 7:
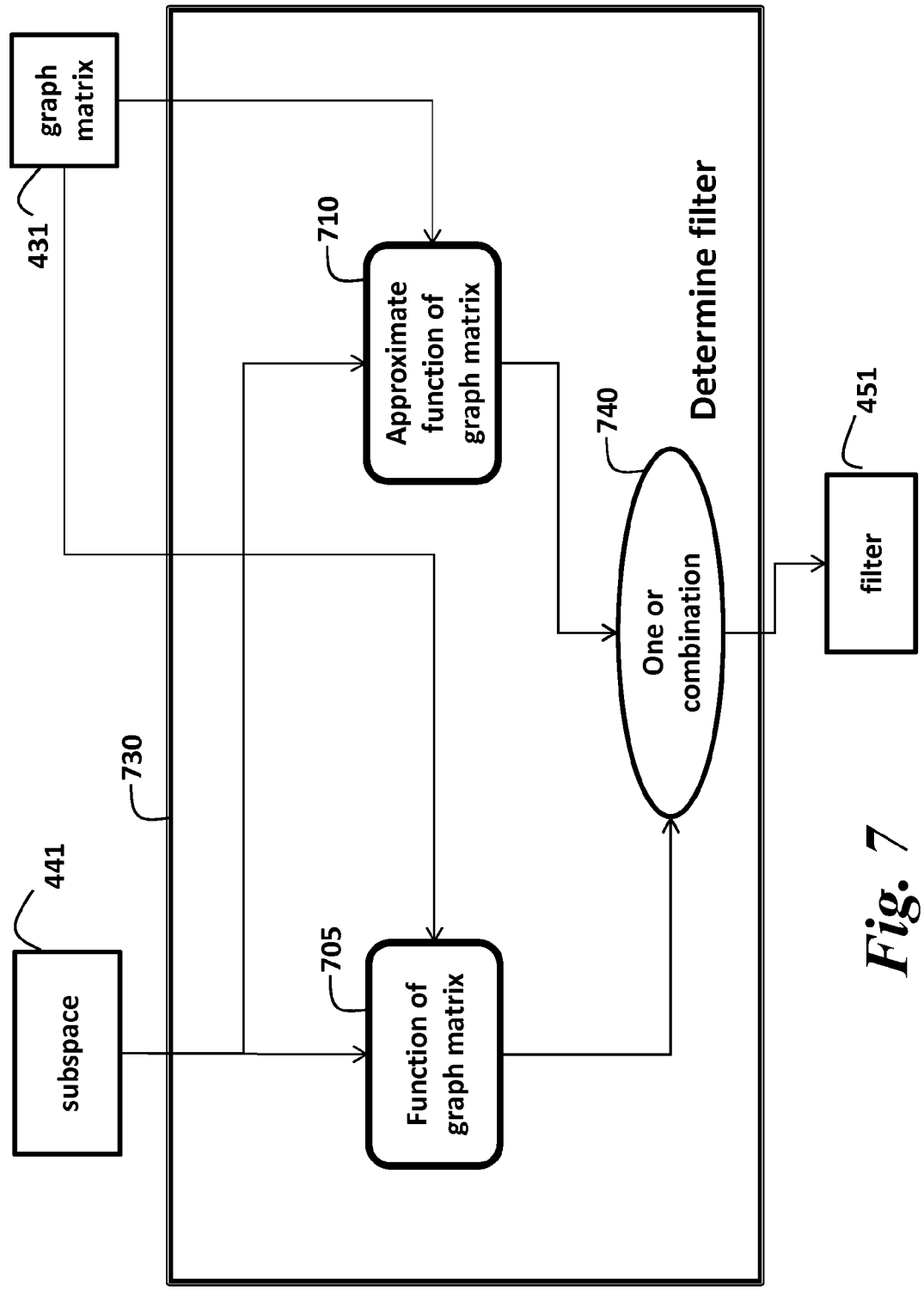
FIG. 7 is a flow diagram of a method for determining a graph filter according to embodiments of the invention.

A value is associated to each node according to a class membership function of a data point or a pixel value. The goal is to reconstruct missing samples of the input signal using the embodiments of this invention. FIG. 4 shows an example for computing the guiding set filter 451 to determine the guiding set used in the method of this invention. Details of the filter are described with reference to FIG. 7.

A graph matrix 431 is determined 430 from the graph as one or a combination of the adjacency matrix and the Laplacian matrix of the graph. In one example application, the type of the graph signal to be interpolated is bandlimited. In this case, we determine 440 a guiding subspace 441 based on the graph matrix and the type 151 of the input signal 130.

A different embodiment determines the guiding set 150 using a range of a guiding transformation, such as a projector, a frame function, and a filter function. The use of the projector is beneficial for frameless reconstruction, wherein, e.g., the dimension of the guiding subspace is too large to store the corresponding frame of the guiding subspace in the memory. The use of the frame function is advantageous when the frame can be easily constructed, and uses a small memory, or the arithmetic operations that perform an action of the frame function on a vector, representing a signal in computer memory, are implemented using optimized for the computer processor Basic Linear Algebra Subprograms (BLAS), such as BLAS-2 and BLAS-3. Implementations involving multiple computer processors, e.g., such as in a graphics processing unit (GPU) using compute unified device architecture (CUDA) or in a field-programmable gate array (FPGA), can be optimized by using corresponding software libraries, such as Scalable Linear Algebra PACKage (ScaLAPACK) and CUDA Basic Linear Algebra Subroutines (cuBLAS).

The use of the filter function to determine the guiding set is beneficial, when constructing the frame or even the projector is impractical. The filter function can, for example, be determined as an approximation using a group comprising a matrix polynomial, an approximate matrix polynomial, a matrix rational function, and an approximate matrix rational function. The matrix polynomial can be determined using a Chebyshev iterative method using one or a combination of roots of Chebyshev polynomials and recursive formulas for the Chebyshev polynomials. Additionally, the matrix polynomial can be determined using a conjugate gradient iterative method.

The matrix polynomial and the matrix rational function are examples of functions of a matrix, wherein the matrix represents the energetic operator, e.g., defined by one or a combinations of natural spectral transforms, such as Fourier, cosine, and wavelet transforms, and transformations obtained by imposed structures, such as the graph Laplacian matrix and the Laplace-Beltrami operator. The use of the polynomials of the matrix is advantageous because their action on a signal can be implemented on a computer processor using a multiplication of the matrix and a vector representing the signal. The use of the rational functions of the matrix as the filter function is advantageous because the rational functions can be constructed to amplify the desired spectral properties of the filter functions, but the rational functions action on a signal typically requires solving a linear system with the matrix, wherein the right-hand side of the system is a vector representing the signal.

Figure 6:
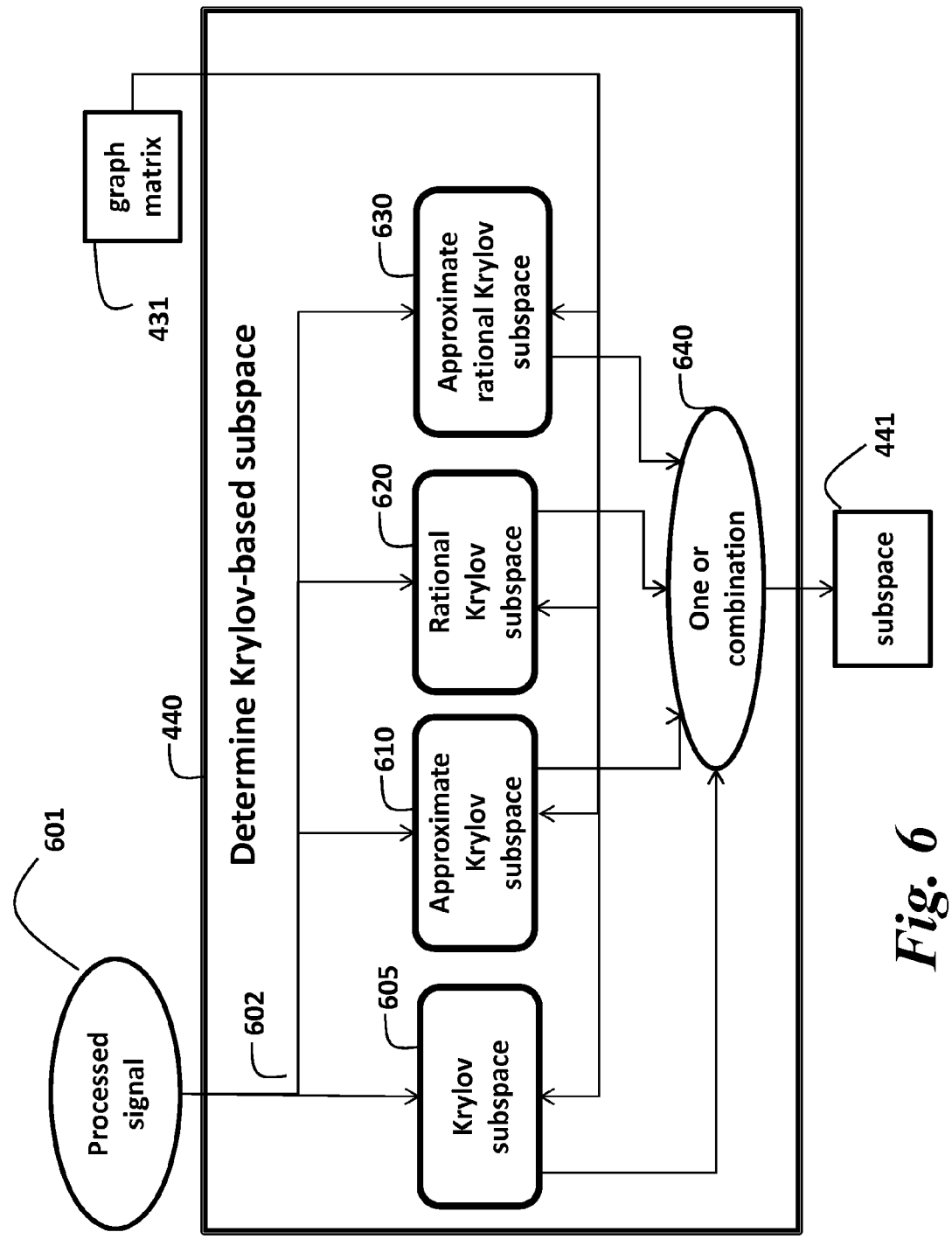
FIG. 6 is a flow diagram of an embodiment of the determining of the Krylov-based subspace according to embodiments of the invention.

In one embodiment, the guiding subspace is a Krylov-based subspace is determined 440, see FIG. 6, as a Krylov-based subspace 441, selected from the group consisting of a Krylov subspace 605, an approximate Krylov subspace 610, a rational Krylov subspace 620, an approximate rational Krylov subspace 630, and combinations 640 thereof. The use of the Krylov subspace is advantageous because it can be constructed using the polynomial of the matrix. In order to simplify the computation, the guiding filter 451 can be determined 450 using the guiding subspace 441.

In a different embodiment, the guiding set can be determined by a function of a graph matrix L, for example, h(L). Additionally, see FIG. 7, according to some embodiments of the invention, the filter 451 to be determined 730 can be one or a combination 740 of a function 705 of a graph matrix L and an approximate function 710 of the graph matrix. For example, if the exact function of the graph matrix is given by h(L), then the approximate matrix function can be h(L̃), where the matrix L̃ is an approximation of the matrix L, for example, a reduced accuracy representation of L, while the function h( ) remains the same.

The filter can, for example, be determined 730 using a matrix polynomial that optimally suppresses graph Fourier spectral components of the signal on an interval, while emphasizing the graph Fourier spectral components outside of the interval. In one embodiment, the polynomial is a Chebyshev polynomial with a predefined stop band that optimally and uniformly suppresses graph Fourier spectral components of the signal above the band, while emphasizing the graph Fourier spectral components below the band.

In a similar embodiment, the polynomial is a combination of polynomials suppressing graph Fourier spectral components of the signal on one or more non-interlacing intervals, while emphasizing the graph spectral components outside of the one or more non-interlacing intervals. For example, the polynomial can be a product of Chebyshev polynomials on corresponding intervals. In another example, the polynomial can be determined that optimally and uniformly suppresses graph Fourier spectral components of the signal on one or more non-interlacing intervals, while emphasizing the graph spectral components outside of the one or more non-interlacing intervals.

One embodiment determines the guiding filter function based on a two-term Chebyshev iterative method using roots of Chebyshev polynomials. Another embodiment utilizes recursive formulas for the Chebyshev polynomials, leading, for example, to a three-term Chebyshev iterative method.

In a different embodiment, the guiding polynomial is adaptive to the signal, wherein adaptive means that the polynomial coefficients or roots are determined dependently on the signal. In one embodiment, an example of the adaptive polynomial is a parameter free adaptive filtering approach that uses iterations of a conjugate gradient (CG) procedure. The guiding CG adaptive filter can be viewed as an example of a Krylov subspace polynomial approximation of an embodiment, where the matrix rational function is based on an inverse of the matrix, or on a pseudo inverse, if the matrix is singular.

Alternatively, or additionally, the transformed signal can be determined directly based on an iterative method that minimizes the function, wherein the number of iterations of the iterative method is determined by a threshold. If the function is quadratic, then the minimization is equivalent to solving a system of linear equations, reflecting the fact that a gradient of the function vanishes at the point of the minimum. Using the iterative method for the function minimization is advantageous because limiting the number of iterations of the iterative method minimizing the function allows the user to control both the filter quality and the computational costs. For example, for the purpose of low pass filtering, one can target the low band in the spectrum. If the number of iterations is too large, then the filter method is computationally complex and restricts the filtering specifically to the selected target, decreasing the filter quality.

Examples of iterative methods minimizing the function include Krylov subspace and rational Krylov subspace methods. In one embodiment, the Krylov subspace methods are, for example, a Lanczos or the conjugate gradient methods, wherein the roots and the coefficients of polynomials adapt to the signal, having the following advantages. The number of iterations required for convergence of CG method is small compared to a projection onto convex sets (POCS) based approach. Thus, the running time decreases substantially, allowing for the proposed signal reconstruction method to reconstruct signals in real time, wherein the sample signal is steaming. The quality of the solution obtained with a given limited number of iterations can be better than POCS based method.

Problem Formulation

In one embodiment of the method, consider a problem of determining a reconstruction $z \in H$ 180 of an unknown original signal $f \in H$ 100 in a Hilbert space H, equipped with a scalar product and a corresponding norm $\|\cdot\|$, from a sample 130 of f, defined as an orthogonal projection Sf onto a closed subspace $S \subseteq H$, called the sampling subspace, wherein the action of the projector S represents the sampling procedure 110. The norm $\|\cdot\|$ determines the similarity measure between the signals.

The original signal f 100 is typically unknown, only the sampled original signal Sf 130 is available as an input to a reconstruction method. Since sampling procedure 110 involves loss of information, we need some a priori assumptions on the original signal f 100 to be recovered.

One such assumption is that the signal f 100 belongs to a closed subspace $T \subseteq H$ that can be thought of as a target reconstruction subspace. We prefer to call T a guiding reconstruction subspace 150, since in our technique, the signal f is not necessarily restricted to T.

Another possible assumption is that the signal f belongs to a compact subset 150 of H, determined by the smoothness of the signal f. In any case, the desired reconstruction minimizes the reconstruction error $\|z-f\|$.

A set of all signals, having the same sample Sf is a closed plane $Sf+S^\perp$ that we call a consistent plane, where $S^\perp$ is the orthogonal complement to the sampling subspace S. But $Sf+S^\perp$ and T generally do not intersect, in which case no reconstructed signal y 180 can be constrained to both sets 140 and 150.

Let T and S be the orthoprojectors onto the closed subspaces T and S respectively. Let $T^\perp = I-T$ and $S^\perp = I-S$, where I is the identity operator, denote the orthoprojectors onto their orthogonal complements $T^\perp$ and $S^\perp$. Let R(A) denote the range of the operator A, and N(A) the null space of R(A), then for any subspace S with projector S, $S=R(S)$ and $S^\perp = R(S^\perp) = N(S)$.

We sample an element $f \in H$ by its projection on S, i.e., the observed sample is given by Sf, and want to reconstruct f from Sf. The signal f can be split into two orthogonal components:

$$f = Sf + x, \text{ where } Sf \in R(S) \text{ and } x \in R(S^\perp), \quad (1)$$

where Sf is the observed sample 130 of f 100 and x contains the missing information to be determined.

A consistent reconstructed signal y can be determined as a solution of the following constrained minimization problem $$\inf_y \|y - Ty\| \text{ subject to } Sy = Sf, \quad (2)$$

which is equivalent, introducing x=y−Sf, to problem $$\inf_{x \in S^\perp} < (x + Sf), T^\perp(x + Sf) >. \quad (3)$$

Problem (3) can be equivalently written in the following operator form, $$(S^\perp T^\perp)|_{S^\perp} x = -S^\perp T^\perp Sf, \quad (4)$$

where $(\cdot)|_{S^\perp}$ denotes the operator restriction to its invariant subspace $S^\perp$ (i.e., the domain of $S^\perp T^\perp$ is restricted to $S^\perp$). If x is a solution to problem (4), then the signal y=x+Sf satisfies $$S^\perp T^\perp y = 0 \text{ and } Sy = Sf, \quad (5)$$

which is an operator form of our constrained minimization problem in equation (2).

In FIG. 3, the signal y corresponds to the first endpoint 212 in the consistent set. The above description specifies how the first endpoint can be determined by the system of equations (4). To compute the second endpoint 230 in FIG. 3, it suffices to multiply y by the orthogonal projector T yielding the signal $y_g$. Another approach to determine $y_g$ is to solve the system of equations $$TSTy = TSf,$$

Using, for example, a conjugate gradient iterative method and then computing $$y_g = Ty.$$

A shown in FIG. 3, the first endpoint 212 is a minimizer of a distance from an element of the consistent plane Sf+$S^\perp$ to the guiding subspace T, while the second endpoint 230 is an element from the guiding subspace T, minimizing the distance to the consistent plane Sf+$S^\perp$.

Equalities Hold $$\min_{y \in Sf+S^\perp} \min_{t \in T} \|y - t\| = \min_{y \in Sf+S^\perp, t \in T} \|y - t\| = \min_{t \in T} \min_{y \in Sf+S^\perp} \|y - t\|,$$

that give us a hint to define a reconstruction set R 160, which is a shortest pathway set between the consistent plane Sf+$S^\perp$ and the guiding subspace T.

Consequently, the reconstruction set R 160 can be determined by a parameter α as the set of all signals $y_\alpha$ spanning the convex linear interval between y and $y_g$, such that $$y_\alpha = \alpha y + (1-\alpha) y_g, \text{ where } 0 \leq \alpha \leq 1.$$

The choice of a particular parameter $\alpha^*$, that minimizes a transforming function, determines the transformed signal 180. For example, determining the reconstruction from noisy or otherwise inaccurate sample, where Sf is substituted by Sf+n, and n represents a deviation from the true sample Sf, we can select $$1 - \alpha = \frac{\|n\|}{\|y - y_g\|}. \quad (6)$$

In equation (6), the numerator $\|n\|$ may be known from specifications of a sampling sensor. The denominator $\|y - y_g\|$ is the diameter of the reconstruction set R 160.

Moreover, the parameter α can also be selected to within a tolerance $T_5$, such that $$\left| 1 - \alpha - \frac{\|n\|}{\|y - y_g\|} \right| \leq T_5.$$

Finally, the reconstructed signal z 170 is determined to be within a distance $d_3$ from $y_\alpha$.

Another formulation of the problem uses a weighted constrained minimization $$\inf_y \|W(y - Ty)\| \text{ subject to } Sy = Sf, \quad (7)$$

which is equivalent, introducing x=y−Sf, to problem $$\inf_{x \in S^\perp} < (x + Sf), W * WT^\perp(x + Sf) >. \quad (8)$$

The operator form of the problem in (8) can be equivalently written as $$(S^\perp T^\perp W * WT^\perp)|_{S^\perp} x = -S^\perp T^\perp W * WT^\perp Sf, \quad (9)$$

Again, if x is a solution to the above problem, then the signal y=x+Sf satisfies $$S^\perp T^\perp W * WT^\perp y = 0 \text{ and } Sy = Sf, \quad (10)$$

which is an operator form of our weighted constrained minimization problem in equation (7).

One embodiment relaxes the constraint that the reconstructed signal y 180 is close to the transformed signal 170 in the reconstruction set 160 and instead uses a weighted unconstrained minimization $$\inf_y c_1 \|W(y - Ty)\| + c_2 \|Sy - Sf\| + E(y), \quad (11)$$

wherein the real positive constants $c_1$, $c_2$, and $c_3$ represent the weights, the expression dist(y,R) denotes a similarity measure between the reconstructed signal y 180 and the reconstruction set R 160, and the function E(y) represent, e.g., an energy of the signal y, or a ratio of a cost over a quality of the reconstruction.

Examples of Signal Reconstruction

The signal reconstruction method and system can be applied to different types of signals. In this section, we elaborate on signal reconstruction for some applications, e.g., graph signal interpolation, image upsampling, and object tracking. It shall be noted that the invention is not limited to these exemplary applications.

For example, the input signal can be an image, a patch in an image, a set of images, a video sequence, a patch in a video sequence, a depth or spectral map, a patch of a depth or spectral map, or image-related feature vectors.

In the acoustic domain, the input signal can be one or a set of audio sequences, such as speech, patches in audio sequences, audio spectral maps, patches of audio spectral maps, and audio feature vectors. Moreover, the method can be applied to a signal that is composed of the combination of an image sequence and an audio sequence.

The input signal can also be one or a set of time series, patches in time series, or time series feature vectors, and combinations thereof.

Image Super-Resolution Upsampling

Figure 5:
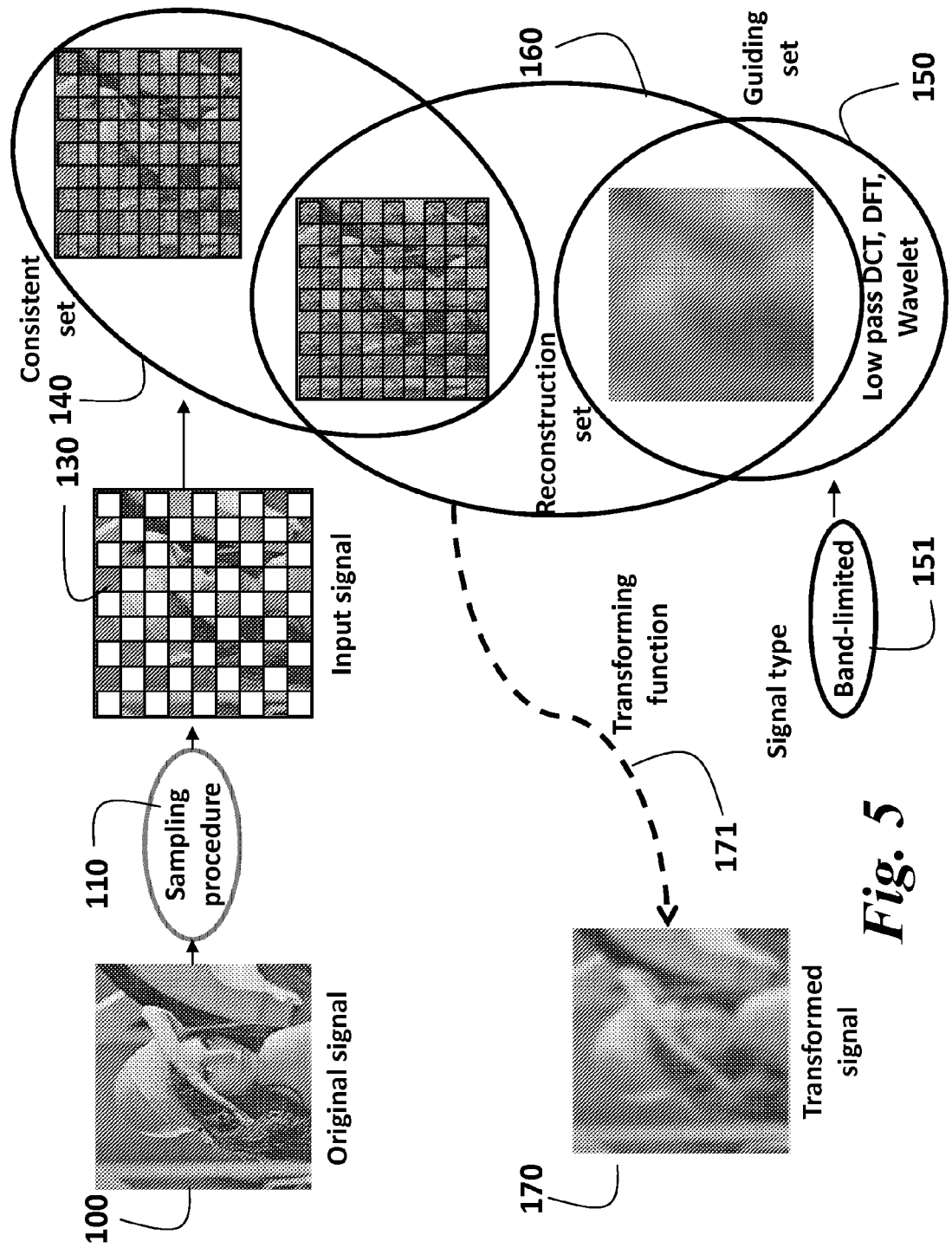
FIG. 5 is a schematic of an application of the method described in this invention for image super-resolution upsampling according to embodiments of the invention.

The image super-resolution upsampling problem represents a simple example for using the method of this invention. FIG. 5 shows an example of upsampling an image using this invention. In original image 100 is sampled using a sampling procedure 110 to obtain an input signal 130. The input signal and the sampling procedure determine a consistent set 140. The consistent set contains images which when sampled using the sampling procedure result in the input signal.

In one embodiment, a type 151 of the input signal is assumed to be bandlimited. The bandlimitedness condition allows us to specify a guiding subspace characterized by one or a combination of low pass discrete cosine transform (DCT), discrete Fourier transform (DFT), discrete wavelet transform (DWT). A collection of images that have coefficients in the DCT, DFT, or DWT domains that are limited to a frequency band constitute a guiding set 150. A reconstruction set 160 can then be determined as the interval having the minimum distance between the consistent set and the guiding set. A transforming function 171 is then minimized to determine the transformed signal 170

Audio Reconstruction

Similar to image upsampling, in acoustic signal or audio reconstruction, the signal includes one or a set of audio sequences, patches in audio sequences, audio spectral maps, patches of audio spectral maps, audio feature vectors. The signal can also include the combination of a video sequence and a corresponding audio track. In this case, the reconstruction problem aims at expanding the bandwidth of narrowband audio signals. The guiding subspace can be obtained by learning from a database of relevant signals. The reconstruction method then finds a reconstructed signal that lies in an interval between the sampling subspace and the guiding subspace. This approach is motivated by a realization that in practical applications it may be difficult to explicitly find a frame of or even choose a reliable target reconstruction subspace. Thus, the guiding subspace is only used as a guide, placing more emphasis on the sampling and a function that characterizes a property of the type of the signal, such as, periodicity.

Object Tracking

One embodiment of the invention tracks interest point descriptors corresponding to different moving objects in a video by identifying the subset of feature descriptors associated only with the objects using a class label.

Figure 8:
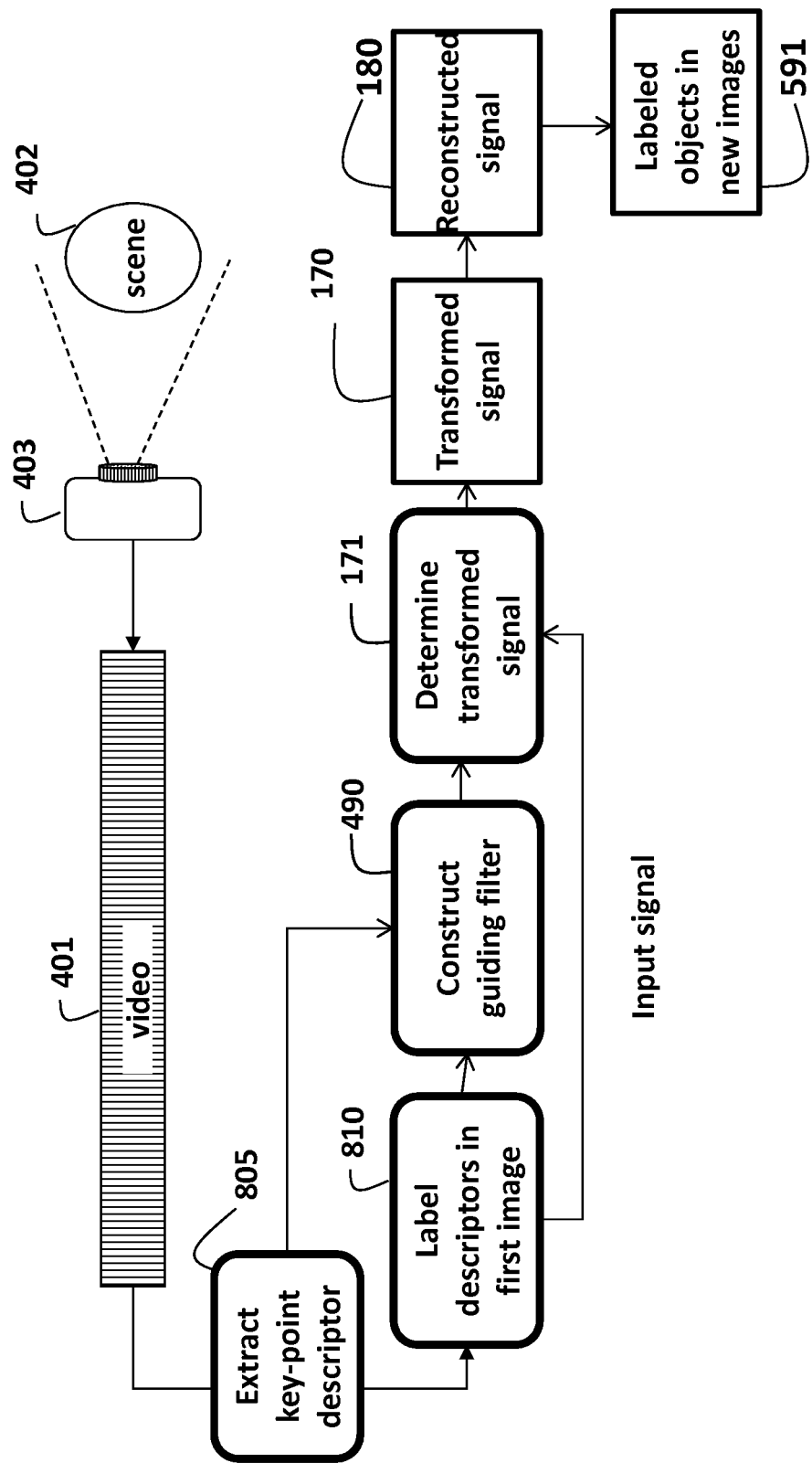
FIG. 8 is a schematic of a method and system for determining object labels in a semi-supervised learning application, such as object tracking according to embodiments of the invention.

FIG. 8 shows a video 401 of a scene 402 acquired using a camera 403. The video is processed to extract interest point feature descriptors 805. Only the descriptors in an initial section of the signal, e.g., the first image in the video, are labeled 810, e.g., manually, such that, the descriptors belonging to the target object are assigned a label value that is different from the descriptors of the rest of the scene. The task is to assign labels to the descriptors in the following video images so that only the descriptors of the target object are assigned the same label value as in the first frame, and all remaining descriptors are assigned a different label.

In one embodiment, the descriptors of the first video image and the next video images are treated as nodes in a graph, and the labels are considered a value of each node, as in the embodiment described for FIG. 4. Using the embodiment for guiding filter construction 490 for graph signal interpolation shown in FIG. 4, a transformed signal 170 is determined 171 according to the guiding filter and the input signal. A reconstructed signal 180 is then determined from the transformed signal using a post processing and label refinement function. The labels of the descriptors in each of the new video images that have a value that matches the value of the labels of the object in the first frame are considered to belong to the object. The locations of those descriptors with the object labels determine the location of the object in the new video images.

Although the invention has been described by way of examples of preferred embodiments, it is to be understood that various other adaptations and modifications can be made within the spirit and scope of the invention. Therefore, it is the object of the appended claims to cover all such variations and modifications as come within the true spirit and scope of the invention.

We claim:

1. A method for reconstructing a signal, wherein the signal is a light field, comprising steps of:
   sampling, using a sampling procedure, the signal to obtain an input signal, wherein the input signal is associated with a type;
   determining a consistent set from the input signal, wherein the consistent set includes first elements such that applying the sampling procedure to the first elements results in the input signal;
   determining, according to the type, a guiding set, wherein the guiding set includes second elements disjoint from the first elements;
   generating a reconstruction set, wherein the reconstruction set includes third elements, wherein the third elements minimize a sum of a first similarity measure of the third elements to the second elements and a second similarity measures of the third elements to the first elements;
   determining a transformed signal that minimizes a function on the reconstruction set;
   generating a reconstructed signal so that a third similarity measure of the reconstructed signal to the transformed signal is smaller than a tolerance; and
   rendering the reconstructed signal, wherein the input signal, the consistent set, the guiding set, the reconstruction set, the transformed signal and the reconstruction signal are stored in a memory connected to a processor performing the steps.

2. The method of claim 1, wherein the type of the input signal is selected from a group consisting of an image, a patch in an image, a set of images, a video sequence, a patch in a video sequence, a depth map, a spectral map, a patch of a depth map, a patch of a map, image-related feature vectors, and combinations thereof, and further comprising:
   determining the guiding set, wherein the determining is selected from a group consisting a Fourier transform, a cosine transform, a wavelet transform, a method for learning from a training dataset, and a spectral transform of a matrix of a graph and combinations thereof, and further comprising:
   constructing the graph according to the type; and
   determining the matrix of the graph using the graph and the input signal.

3. The method of claim 1, wherein the input signal is streaming, further comprising steps of:
   generating the reconstructed signal in real time.

4. The method of claim 1, wherein one or a combination of the type, the consistent set, and the guiding set is determined using a first set of probability distributions, and further comprising:

determining the reconstruction set using a second set of probability distribution using a statistical similarity measure between stochastic random variables according to the first set of the probability distributions.

5. The method of claim 1, wherein one or a combination of the consistent set and the guiding set comprises one or a group of first linear sets, and further comprising:
determining the reconstruction set using a second linear set according one or the group of the first linear sets.

6. The method of claim 5, wherein the guiding set is a Krylov-based subspace selected from a group consisting of an approximate Krylov subspace, a rational Krylov subspace, an approximate rational Krylov subspace, and combinations thereof, and further comprising:
determining the reconstruction signal using a Krylov-based method according to the Krylov-based subspace.

7. The method of claim 5, further comprising:
determining the guiding set using a range of a guiding transformation, comprising one or a combination of a projector, a frame function, and a filter function.

8. The method of claim 7, further comprising:
approximating the filter function using one or a combination of a matrix function or an approximate matrix function, wherein the matrix function is determined using a group consisting of a matrix polynomial, an approximate matrix polynomial, a matrix rational function, an approximate matrix rational function, and combinations thereof.

9. The method of claim 8, further comprising:
determining the matrix polynomial using a Chebyshev iterative method using one or a combination of roots of Chebyshev polynomials and recursive formulas for the Chebyshev polynomials.

10. The method of claim 1, further comprising:
determining at least one of the first, second, and third similarity measures using one or a combination of a distance, a norm, a semi-norm, a correlation, a coherence, a divergence, and a metric.

11. The method of claim 1, further comprising:
determining the function using the first similarity measure, the second similarity measure, and a parameter, such that a ratio of the first similarity measure to the second similarity measure equals the parameter at a minimum of the function.

12. The method of claim 11, wherein the sampling procedure causes an inaccuracy in the input signal due to one or a combination of noise, a limited accuracy of a sensor used by the sampling procedure, and a limited precision of the input signal, further comprising:
determining a level of the inaccuracy in the input signal relative to a diameter of the reconstruction set; and
determining the parameter to be proportional to the level of the inaccuracy.

13. The method of claim 1, wherein the reconstruction set is an interval with a first endpoint in the consistent set, and a second endpoint in the guiding set, and further comprising:
determining the first endpoint using one or a combination of solving a first system of equations and projecting the second endpoint to the consistent set;
determining the second endpoint using one or a combination of solving a second system of equations and projecting the first endpoint to the guiding set;
determining the reconstruction set as a convex linear combination of the first endpoint and the second endpoint; and solving one or a combination of the first system of equations and the second system of linear equations using an iterative method.

14. The method of claim 13, wherein the transformed signal is determined using an iterative method that minimizes the function, and further comprising:
adjusting a termination criteria of the iterative method using a training dataset; and
determining the iterative method using a conjugate gradient iterative method, a Chebyshev iterative method, a preconditioned iterative method, and combinations thereof.

15. The method of claim 2, wherein the signal further includes a sound field and wherein the type of the input signal includes one or a set of audio sequences, patches in audio sequences, audio spectral maps, patches of audio spectral maps, audio feature vectors, and combinations thereof.

16. An apparatus for reconstructing a signal, wherein the signal is a light field, comprising:
at least one sensor for sampling the signal with a sampling procedure to obtain an input signal, wherein the input signal is associated with a type;
a memory for storing the input signal, a consistent set determined from the input signal, wherein the consistent set includes first elements such that applying the sampling procedure to the first elements of the consistent set results in the input signal, a guiding set of second elements disjoint from the first elements, determined according to the type, a reconstruction set including third elements, wherein the third elements minimize a sum of a first similarity measure of the third elements to the second elements set and a second similarity measures of the third elements to the first elements, a transformed signal that minimizes a function on the reconstruction set, a reconstructed signal so that a third similarity measure of the reconstructed signal to the transformed signal is smaller than a tolerance;
at least one processor, connected to the memory, performing steps of determining the consistent set, the guiding set and the transformed signal, and generating the reconstruction set and the reconstruction signal; and
at least one output device, rendering the reconstructed signal.

17. The apparatus of claim 16, wherein the signal comprises a light field and the type is selected from a group consisting of an image, a patch in an image, a set of images, a video sequence, a patch in a video sequence, a depth map, a spectral map, a patch of a depth map, a patch of a map, image-related feature vectors, one or a set of audio sequences, patches in audio sequences, audio spectral maps, patches of audio spectral maps, audio feature vectors, a set of time series, patches in time series, time series feature vectors, and combinations thereof, and wherein the at least one processor determines the guiding selected from a group consisting of a Fourier transform, a cosine transform, a wavelet transform, a method for learning from a training dataset, and a spectral transform of a matrix of a graph and combinations thereof, wherein the graph is constructed according to the type of the input signal and the matrix of the graph is determined using the graph and the input signal.

18. The apparatus of claim 16, wherein the input signal is streaming and the reconstructed signal is generated in real time.

19. A method for reconstructing a signal, wherein the signal is a light field, comprising steps of:

sampling, using a sampling procedure, the signal to obtain an input signal associated with a type;

determining a consistent set from the input signal, wherein the consistent set including first elements such that applying the sampling procedure to the first elements of the consistent set results in the input signal;

determining, according to the type, a guiding set of second elements disjoint from the first elements;

generating a reconstruction set including third elements, wherein the third elements minimize a combination of a first similarity measure of the reconstructed signal to the guiding set, a second similarity measure of the reconstructed signal to the consistent set and a function of property of the reconstructed signal;

determining a transformed signal that minimizes a function on the reconstruction set;

generating a reconstructed signal so that a third similarity measure of the reconstructed signal to the transformed signal is smaller than a tolerance; and rendering the reconstructed signal, wherein the input signal, the consistent set, the guiding set, the reconstruction set, the transformed signal and the reconstruction signal are stored in a memory connected to a processer performing the steps.

20. A method for reconstructing a signal, wherein the signal represents object labels in one or a combination of a time varying light field, an image sequence, and a video sequence, comprising:

determining an input signal using labels for interest points of different objects in an initial section of the signal;

determining a graph and an associated graph matrix that connects the interest points across the signal;

determining a type according to the graph matrix;

determining a consistent set from the input signal, wherein the consistent set includes first elements such that applying the sampling procedure to the first elements of the consistent set results in the input signal, a guiding set of second elements disjoint from the first elements, determined according to the type, a reconstruction set including third elements, wherein the third elements minimize a sum of a first similarity measure of the third elements to the second elements set and a second similarity measures of the third elements to the first elements, a transformed signal that minimizes a function on the reconstruction set, a reconstructed signal so that a third similarity measure of the reconstructed signal to the transformed signal is smaller than a tolerance;

outputting labels to unlabeled objects in the signal using the reconstructed signal.

* * * * *